United States Patent [19]
Balch et al.

[11] Patent Number: 5,746,901
[45] Date of Patent: May 5, 1998

[54] HYBRID SLAB-MICROCHANNEL GEL ELECTROPHORESIS SYSTEM

[75] Inventors: Joseph W. Balch; Anthony V. Carrano; James C. Davidson, all of Livermore; Jackson C. Koo, San Ramon, all of Calif.

[73] Assignee: Regents Of The University Of California, Oakland, Calif.

[21] Appl. No.: 628,309

[22] Filed: Apr. 5, 1996

[51] Int. Cl.$^6$ .................... G01N 27/26; G01N 27/447
[52] U.S. Cl. .................... 204/606; 204/456; 204/466; 204/616
[58] Field of Search .................. 204/606, 607, 204/608, 609, 610, 612, 613, 614, 615, 616, 617, 618, 619, 620, 621, 605, 456, 457, 458, 459, 461, 462, 463, 464, 465, 466, 467, 470, 455

[56] References Cited

U.S. PATENT DOCUMENTS

| | | | |
|---|---|---|---|
| 4,417,967 | 11/1983 | Ledley | 204/466 |
| 4,762,743 | 8/1988 | von Alren et al. | 204/620 X |
| 5,047,135 | 9/1991 | Nieman | 204/619 |
| 5,071,531 | 12/1991 | Soane | 204/616 |
| 5,192,412 | 3/1993 | Kambara et al. | 204/612 |

OTHER PUBLICATIONS

UCRL–119660, J.W. Balch et al., "Advanced Microinstrumentation for Rapid DNA Sequencing and Large DNA Fragment Separation", 1995.

*Primary Examiner*—Kathryn L. Gorgos
*Assistant Examiner*—John S. Starsiak, Jr.
*Attorney, Agent, or Firm*—L. E. Carnahan; Henry P. Sartorio

[57] ABSTRACT

A hybrid slab-microchannel gel electrophoresis system. The hybrid system permits the fabrication of isolated microchannels for biomolecule separations without imposing the constraint of a totally sealed system. The hybrid system is reusable and ultimately much simpler and less costly to manufacture than a closed channel plate system. The hybrid system incorporates a microslab portion of the separation medium above the microchannels, thus at least substantially reducing the possibility of non-uniform field distribution and breakdown due to uncontrollable leakage. A microslab of the sieving matrix is built into the system by using plastic spacer materials and is used to uniformly couple the top plate with the bottom microchannel plate.

19 Claims, 1 Drawing Sheet

HYBRID SLAB-MICROCHANNEL GEL ELECTROPHORESIS SYSTEM

The United States Government has rights in this invention pursuant to Contract No. W-7405-ENG-48 between the United States Department of Energy and the University of California for the operation of Lawrence Livermore National Laboratory.

BACKGROUND OF THE INVENTION

The present invention relates to electrophoresis systems, particularly to electrophorectic separations of biomolecules, and more particularly to means such as a hybrid slab-microchannel gel arrangement in an electrophoresis system which reduces perturbations in the electric field and leakage currents.

Electrophoresis involves the separation of charged ions or molecules based on their differential migration in an applied electric field. It is a widely used technique in biochemistry for separating biomolecules. Electrophoresis systems are typically comprised of a sieving matrix (i.e. polyacrylamide gel) sandwiched between two plates of glass. Such a slab gel system is exemplified by U.S. Pat. No. 5,047,135 issued Sep. 10, 1991 to E. Nieman.

Many clinical, molecular, or forensic projects that involve the characterization of DNA are dependent upon the separation and/or purification of DNA fragments by one or more methods. A common method is based upon electrophoresis. Since the DNA double-helix backbone is negatively charged, fragments of DNA migrate toward the anode when placed in an electric field. If the DNA is cause to migrate through a sieving matrix such as agarose or polyacrylamide, fragment mobility is a function of fragment size, i.e., the smaller fragments migrate faster than larger fragments. The different sieving matrices available and methods of applying the electric field offer variables for adapting the electrophoresis procedure to suit specific needs.

The techniques of DNA sequencing (the process of determining the order of nucleotides in a DNA molecule) and large DNA fragments analysis are both highly valued by many clinical, molecular biology and forensic projects. Sequencing the human genome will help provide an understanding and potential treatment of genetic disorders. For example, genes for the following disorders have recently been identified: Multiple Sclerosis, Amyotrophic Lateral Sclerosis, and Huntington's disease. Typical applications of fragment analysis and collection include: 1) restriction fragment analysis to trace disease-associated DNA polymorphisms through family members: 2) DNA fingerprinting to detect common fragments in the evaluation of DNA identity for forensics or to establish commonalty between cloned segments of DNA; and 3) Southern analysis which involves the hybridization of molecular probes onto the separated DNA fragments to determine the precise location of a gene of interest.

Major limitations of current DNA electrophoresis analysis systems include the time required to run a sample by electrophoresis and the number of electrophoresis channels (lanes) that can be run simultaneously. For example, the separation of double-stranded (undenatured) DNA fragments in the range of about 100 to 20,000 base pairs (bp) are best fractionated by embedding them in an agarose gel sieving matrix and applying a constant voltage across the gel. Such electrophoretic separations usually take about 2-12 hours. Likewise, DNA sequence analysis in an Applied Biosystems (ABI) Model 373 automated DNA sequencer requires approximately 10 hours to separate and identify 500 bases of sequence information per lane. Typically fragments are run in up to 36 parallel lanes. Thus, this state-of-the-art commercial DNA sequencer has a maximum throughput of 1800 bases per hour. At this rate, more than 1.7 million hours of separations will be required to sequence the 3 billion bases in the human genome—assuming 100% yield and not allowing for any repeat experiments. Newer model sequencers (e.g. Applied Biosystems Model 377) may increase the throughput by a factor of two.

For some time it has been recognized that the use of thinner gels in electrophoresis would allow faster separations. Current DNA sequencers such as the ABI 373 use 0.3–0.4 mm thick slab gels which have relatively poor thermal dissipation of the joule heating created by the current flow in the gel. To limit the thermal dispersion of the separated fragments in these gels, the temperature variation across the thickness of the gel must be less than 1° C. which requires limiting the electric field to a maximum of approximately 50 V/cm in conventional slab gel instruments. By doing the separations in thinner gels whose joule heating can be more quickly dissipated, the electric field can be increased, resulting in shorter separation times. The advantages of thinner gels in allowing high-speed separations of DNA from sequencing reactions has recently been demonstrated by several groups using gel-filled capillary electrophoresis. In gel capillary electrophoresis the separation is typically done in a 50–100 um internal diameter quartz capillary which has much improved thermal dissipation over thicker slab gels. For example, using a 50 um i.d. capillary operated at an electric field of 200 V/cm, there has been demonstrated a ten-fold reduction in separation time of a DNA sample compared to the separation time required for the same sample using the ABI 373 DNA sequencer operated with a 400 um thick slab gel and run with a 30–37.5 V/cm applied electric field. Efforts to develop high-speed, high throughput automated DNA sequencers by combining many small diameter quartz capillaries (e.g. 10–100) have experienced many mechanical and electrical problems concerned with: 1) filling multiple capillaries with equally high quality gel; 2) loading the DNA samples into separate capillaries; and 3) devising a sensitive optical detection system to measure the output fluorescence signals from all the very small capillaries. Other major factors limiting resolution of DNA fragments by electrophoresis include sample quality, sample loading on to the gel, and diffusion of DNA through the gel prior to the time of detection. Recent progress in using pumpable low viscosity polymer sieving media may greatly reduce the problems of filling multiple capillaries systems.

Research and development efforts are being carried out at the Lawrence Livermore National Laboratory (LLNL), University of California, to develop a rapid DNA sequencing and large fragment analysis technology based upon gel electrophoresis. This development involves efforts to: 1) build a high density array of electrophoresis lanes on a single substrate for DNA sequencing and large fragment separation; and 2) build an ultra sensitive fluorescence detection system to image the DNA fragments. See UCRL-ID-119660 Advanced Microinstrumentation for Rapid DNA Sequencing and Large Fragment Separation, J. W. Balch, et al., 1995.

Electrophoresis systems are typically comprised of a sieving matrix (i.e., polyacrylamide gel) sandwiched between two plates of glass. An electric field is applied across the device thus providing the force necessary to separate molecules based upon their mobility in the sieving medium. These plates are usually used repeatedly with only the sieving matrix being replaced between runs. The above-referenced development efforts at LLNL involve microfabrication techniques for the development of high density arrays of electrophoresis microchannels in glass substrates. Thus, one of the two plates of glass of a typical electrophoresis system would be provided with microchannels formed therein, thereby increasing the number of lanes on a single substrate or plate. To produce the desired high density array of electrophoresis lanes, the goal of the microfabrication technique is to provide for the formation of 200 microchannels, each 50 microns wide, 50 microns deep, and spaced 150- microns apart, in a 4 cm by 25 cm area of an electrophoresis plate. However, the number of microchannels may range from about 20–50 per cm. Also, U.S. Pat. No. 5,192,412 issued Mar. 9, 1993 to H. Kambara et al. involves a two plate electrophoresis apparatus wherein one of the glass plates is provided with a plurality of parallel electrophoresis grooves (10/cm), and a groove intersecting the electrophoresis grooves for laser beam irradiation of the fragments passing through the electrophoresis grooves.

As pointed out above, in typical two plate electrophoresis systems, the plates are usually used repeatedly with only the sieving matrix being replaced between runs. It has been found by experimentation that when a similar approach is used with one plate containing microchannels for microgels, problems arise. The experiments show that air bubbles are often trapped and that the gel may not form uniformly where the plates contact each other. Such inclusions and non-uniformity can result in perturbations in the electric field as well as leakage currents which cause local heating and thus undesired diffusion. It has been observed that these effects can also lead to arcing and actual boiling and burning of the matrix material. One alternative to solving this problem is to totally encapsulate the microchannels by bonding the plates together. However, this has a major drawback of being a fixed set of microchannels which will be difficult to clean and reuse with gel matrices, without removing the bonding material between the plates.

The present invention provides another alternative to the above-described problem, without bonding of the plates together. The approach of this invention is to utilize a microslab of the sieving matrix which covers the microchannels and couples the top plate with the bottom microchannel plate, and thus eliminates a need for bonding the plates together to eliminate the above-referenced problems associated with air bubbles trapped in the microchannels. Thus, the present invention provides a hybrid slab-microchannel gel electrophoresis system which at least partially overcomes the above-referenced problems while utilizing the advantages provided by the microchannels to significantly increase the throughput in an electrophoresis system utilizing the same size plates. In the present invention, the microslab of the sieving matrix is built into the system by using plastic spacer materials.

SUMMARY OF THE INVENTION

It is an object of the invention to provide a microchannel electrophoresis system with means for reducing non-uniform field distribution and breakdown due to uncontrollable leakage currents.

A further object of the invention is to provide a hybrid electrophoresis system.

Another object of the invention is to provide a hybrid slab-microchannel gel electrophoresis system which substantially eliminates leakage between the microchannels.

Another object of the invention is to provide a microchannel electrophoresis system with a microslab of the sieving material covering the microchannels.

Another object of the invention is to provide a microchannel electrophoresis system with a microslab of the sieving material used to couple the top plate with the bottom microchannel plate of the system.

Other objects and advantages of the present invention will become apparent from the following description and accompanying drawings. The present invention is basically a hybrid electrophoresis system for reducing leakage between microchannels. The invention incorporates a microslab of separation medium above the microchannel of a microchannel electrophoresis system, thus removing or at least reducing the possibility of non-uniform field distribution, and breakdown due to uncontrollable leakage currents. The microslab of the sieving matrix is built into the system by using plastic spacer materials, such as 25–50 micrometer thick Mylar. The flatness of the two electrophoresis plates should have less than 25 micrometer warpage in the active area of the plates that enclose the microchannels. Biomolecules are loaded into the microchannels (e.g. 50–400 micrometers deep) and are separated as they migrate down the microchannels by the microslab positioned to cover the microchannels. Thus, the microslab functions to couple the top plate with the bottom microchannel plate of the electrophoresis system.

BRIEF DESCRIPTION OF THE DRAWINGS

The accompanying drawings, which are incorporated into and form a part of the disclosure, illustrate an embodiment of the invention and, together with the description, serve to explain the principles of the invention.

DETAILED DESCRIPTION OF THE INVENTION

Figure 1:
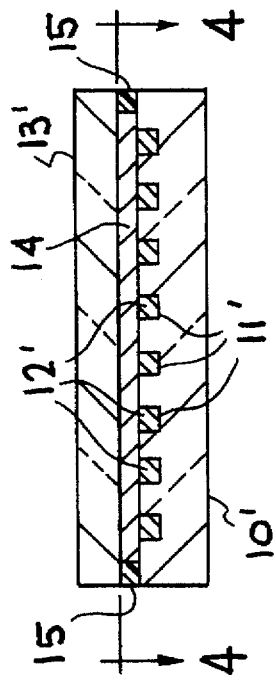
FIG. 1 is a cross-sectional view of a schematic of an embodiment of a microchannel gel electrophoresis device.

The present invention is directed to a hybrid gel electrophoresis device and involves the use of slab gel and microchannel gel. The device permits the fabrication of isolated microchannels for biomolecule separations without imposing the constraint of a totally sealed system. This device is reusable and ultimately much simpler and less costly to manufacture than a closed channel plate system. This device can be used for separation and detection of a large class of biomolecules such as DNA fragments, DNA sequencing ladders and proteins. The invention involves a cost effective method of fabricating multiple use microchannel gel electrophoresis plates. Gel electrophoresis of biomolecules and DNA fragments have commercial application in research, forensics, and clinical diagnostics.

The present invention uses a conventional slab of a sieving matrix having a thickness of 25–50 micrometers sandwiched between two plates of glass, for example, with a bottom plate thereof being provided with longitudinally extending, parallel microchannels, having a depth of 50–400 micrometers, a width of about 50–500 micrometers, and spaced about 500 micrometers apart. The microchannels are formed at a range of about 20–50 per cm of the bottom plate.

The microchannels are filled with a thin electrophoresis gel. The top plate of the device is of an optical quality that will, for example, transmit the laser-induced fluorescence of the fluorochrome labeled DNA fragments onto a sensitive optical detector.

The microchannel arrangement of the present invention is described in the above-referenced UCRL-ID-119660. Various arrays of microchannels for sequencing experiments have been constructed in glass substrates using various techniques including ultrasonic milling, ultrasonic milling plus mechanical polishing, ultrasonic milling plus a final wet chemical polish, and wet chemical etching. Using chemical etching, for example, microchannel arrays were constructed involving 48 microchannel (200 μm deep, 1.25 mm wide, and a 25 cm load-to-read distance). The electrophoresis resolution in these channels was characterized for standard 6% polyacrylamide gel run at an approximate electric field strength of 40 V/cm. Good sequencing resolution was achieved.

The present invention is a hybrid slab microchannel gel electrophoresis system which at least overcomes the above-described leakage problems relative to the use of microchannel for microgels. This invention incorporates a microslab of the separation medium above the microchannels thus reducing the possibility of non-uniform field distribution and breakdown due to uncontrollable leakage currents. A microslab of the sieving matrix (e.g. polyacrylamide gel) is built into the system by using plastic spacer materials (e.g. 25–50 micrometer thick Mylar). The flatness of the two electrophoresis plates should have less than 25 micrometers warpage in the area that encloses the microchannels. Biomolecules are loaded into the microchannels (e.g. 50–400 micrometer deep) and are separated as they migrate down the channel. The microslab is used to uniformly couple the top plate with the bottom microchannel plate. While not shown, buffer reservoirs are located at the ends of the microchannels, and electrodes are provided therefore, as known in the art. While glass has been used as the bottom microchannel plate, other high thermal conductivity substrates or plates may be used, such as a glass-silicon sandwich, glass, ceramic, and plastic. In addition to the sieving matrix of the microslab and in the microchannels being polyacrylamide gel, it may be composed of agarose, polyacrylamide, and entangled polymers. The gel material in the microchannel needs to be the same as the material of which the microslab is composed.

The present invention utilizes an electrically insulated or high resistance, high thermal conductivity substrates to support and encompass microgels used for electrophoretic separations. For example, the thermal conductivity is in the range of 1 to 30 watts/meter-K (vac), and the resistance is in the range of 4 to $10^{10}$ megohm-cm. The microchannels are etched or milled into the substrate or bottom plate, and if the plate is not electrically insulating, it is processed to ensure electrical insulation. Performance is also improved with reduction in the size of the microgels as the effective field strength can be increased in so doing. The total energy dissipated in the gel is reduced as the gel is reduced in size and consequently its resistance increases. Microgels also have an increased surface to volume ratio compared to conventional gels thus improving thermal dissipation. This, in conjunction with high thermal conductivity materials, will greatly enhance the thermal dissipation thus allowing a high field to be applied for faster separations.

Figure 3:
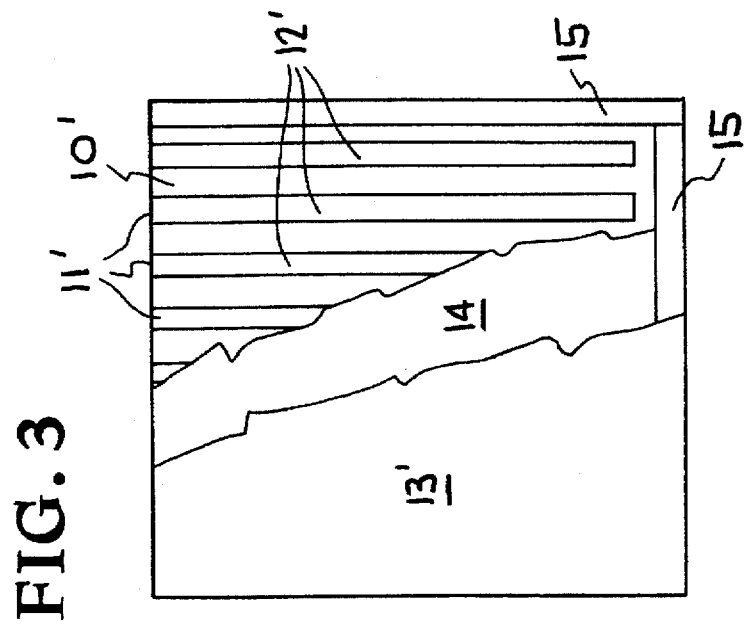
FIG. 3 is a cross-sectional view of a schematic of an embodiment of a hybrid slab-microchannel gel electrophoresis device in accordance with the present invention.
Figure 2:
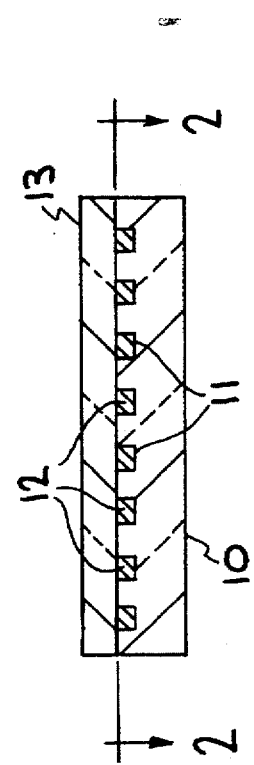
FIG. 2 is a plan view taken along the line 2—2 of FIG. 1 of the bottom microchannel plate.
Figure 4:
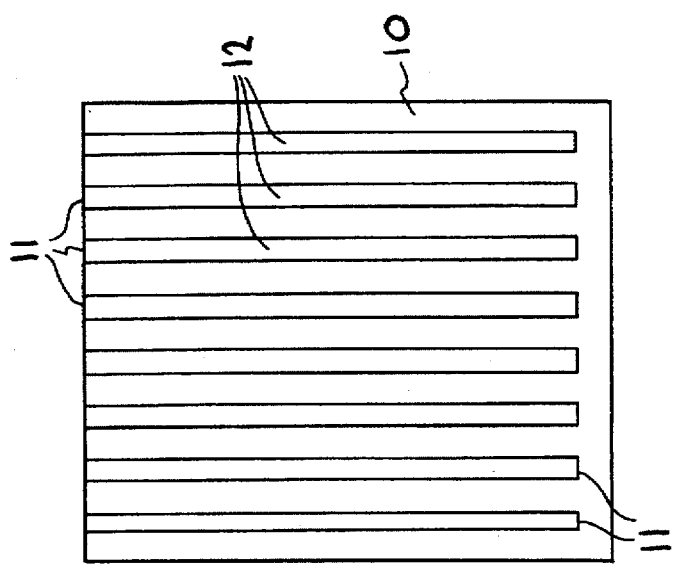
FIG. 4 is a plan view taken along the line 4—4 of FIG. 3 with the microchannels in the bottom plate being shown in phantom.

Referring now to the drawings, FIGS. 1 and 2 illustrate an embodiment of a microchannel electrophoresis device without the microslab of the present invention, while FIGS. 3 and 4 illustrate the microchannel electrophoresis of FIGS. 1 and 2 with the microslab between the top and bottom plates. Basically, the present invention adds to the microchannel device of FIGS. 1 and 2 a microslab of separation material which couples the top plate with the bottom microchannel plate.

As shown schematically in FIGS. 1 and 2, the device comprises a bottom plate or substrate 10 having formed then a plurality of longitudinally extending, parallel microchannels 10, containing a microgel 12, and a top plate 13 of optical quality material. The substrate 10, though not shown, is provided with a pair of electrodes and a pair of buffer reservoirs.

FIGS. 3 and 4 schematically illustrate the hybrid electrophoresis devices of this invention, and like the embodiment of FIGS. 1 and 2 comprises a bottom plate or substrate 10' having parallel longitudinally extending microchannel 11' containing a microgel 12', and a top plate 13' of optical quality material. Interposed between the bottom plate 10' and the top plate 13' is a microslab 14 of separation medium which is secured between the plates by plastic spacers 15 (e.g. 25–50 micrometers wide). The thickness or height of the spacers 15 is dependent on the thickness of the microslab 14, which for example may range from 25 to 100 micrometers, preferably 50 micrometers.

By way of example, the bottom plate or substrate 10' may be constructed of glass, ceramic, glass-on-silicon, or plastic; with a width of 10 cm to 25 cm, length of 25 cm to 50 cm, and thickness or height of 5 mm to 10 mm, with the microchannels 11' therein having a depth of 50 to 400 micrometers, a width of 50 to 500 micrometers, and a spacing of 500 to 1000 micrometers. The microchannels 11' may extend the full length of the bottom plate 10', and thus a buffer reservoir would be provided at each end. The top plate 13' may be constructed of glass, ceramic, glass-on-silicon, or plastic, having a width and length the same as the bottom plate 10', and a thickness of 5 mm to 10 mm. The separation material 12' in the microchannels may be composed of agarose, polyacrylamide, or entangled polymers. The microslab 14 may be composed of the same material as the separation material 12', with a thickness of 25 to 100 micrometers. The composition of the microslab 14 and the material 12' would be the same for each separator. The spacers 15, in addition to being composed of Mylar may be composed of polycarbonate, nylon, or other plastic materials, with the thickness being the same as the thickness of the microslab 14. The microslab 14 is used to couple the top plate 13' with the bottom microchannel plate 10' thereby reducing the above-referenced undesirable leakage between the adjacent microchannels.

It has thus been shown that the present invention, which incorporates a uniform microslab of separation medium between the bottom microchannel plate and the top plate and covers the upper openings of the microchannel serves to reduce, if not eliminate the leakage problems associated with the microchannel electrophoresis systems. Thus, the electrophoresis device of this invention constitutes a hybrid slab-microchannel gel electrophoresis device which provides the advantages of both types of systems.

While a particular embodiment has been illustrated and/or described, with specific materials and parameters to exemplify and explain the principles of the invention, such are not intended to be limiting. Modifications and changes may become apparent to those skilled in the art, and it is intended that the invention be limited only by the scope of the appended claims.

The invention claimed is:

1. A microchannel electrophoresis device having means for reducing current leakage between microchannels, comprising:

a bottom plate having parallel longitudinally extending microchannels in one surface thereof;

a first separation medium located in said microchannels;

a slab of separation medium separate from said first separation medium positioned over said microchannels and the first separation medium therein;

a top plate of optical quality material positioned on said slab of separation medium, and means for retaining the slab of separation medium between said bottom and top plates.

2. The device of claim 1, wherein said microchannels extend the entire longitudinal length of said bottom plate.

3. The device of claim 1, wherein said parallel microchannels have a depth of 50 to 400 micrometers, width of 50 to 500 micrometers, and are spaced apart by a distance of 500 to 1000 micrometers.

4. The device of claim 1, wherein said slab of separation medium has a thickness of 25 to 100 micrometers.

5. The device of claim 1, wherein the separation medium in said microchannels is composed of material selected from the group of agarose, polyacrylamide, or entangled polymers.

6. The device of claim 1, wherein said separation medium of said slab is composed of material selected from the group of agarose, polyacrylamide, or entangled polymers.

7. The device of claim 1, wherein said bottom plate is constructed of material selected from the group of glass, ceramic, glass-on-silicon and plastic.

8. The device of claim 1, wherein said bottom and top plates have a length of 25 to 50 cm and a width of 10 to 25 cm.

9. The device of claim 8, wherein said plates have a width of about 4 cm and a length of about 25 cm, and wherein said bottom plate has 20–50 of said parallel longitudingly extending microchannels per cm.

10. In a microchannel, electrophoresis device having a bottom plate containing separation material in microchannels thereof, the improvement comprising:

a slab of separation material covering the microchannels in said bottom plate and the separation material therein of said device.

11. The improvement of claim 10, wherein said slab has a thickness of 25 to 100 micrometers.

12. The improvement of claim 10, wherein said slab is composed of separation material selected from the group of agarose, polyacrylamide, or entangled polymers.

13. The improvement of claim 10, wherein said slab of separation material is composed of the same separation material as contained in microchannels of the device.

14. In the microchannel, electrophoresis device of claim 10, wherein the microchannels are formed in said bottom plate thereof in a range of about 20–50 per cm.

15. A method for fabricating a microchannel gel electrophoresis device having means for at least reducing leakage between active areas of the microchannels comprising:

providing a bottom plate of electrically insulative material, forming parallel longitudinally extending microchannels in the bottom plate, forming an upper surface of the bottom plate to have a flatness of less than 25 micrometer warpage in the active areas of the microchannels, providing a separation medium in the microchannels, providing a slab of separation medium over the microchannels and the separation medium therein, providing a top plate over the slab of separation medium, and forming the top plate to have a surface adjacent the slab of separation medium to have a flatness of less than 25 micrometer warpage in the active areas of the microchannels.

16. The method of claim 15, wherein the microchannels are formed in the bottom plate in a range of 20–50 per cm of the bottom plate.

17. The method of claim 15, additionally including providing means for retaining the slab of separation medium between the bottom and top plates.

18. The method of claim 17, wherein said means is formed by spacers positioned between the top and bottom plates and at least two of the edges of the slab of separation medium.

19. The method of claim 15, additionally providing the bottom plate from material selected from the group of glass, ceramic, glass-on-silicon, and plastic; and wherein the top plate is composed of optical quality material.

* * * * *